United States Patent
Ljungmann et al.

(10) Patent No.: US 7,998,408 B2
(45) Date of Patent: Aug. 16, 2011

(54) APPARATUS FOR EXECUTION OF TREATMENT OPERATIONS ON MICROSCOPE SLIDES WITH TISSUE SPECIMENS

(75) Inventors: Øystein Ljungmann, Siggerud (NO); Torstein Ljungmann, Nesoddtangen (NO)

(73) Assignee: Dako Instrumec AS, Oslo (NO)

( * ) Notice: Subject to any disclaimer, the term of this patent is extended or adjusted under 35 U.S.C. 154(b) by 743 days.

(21) Appl. No.: 11/793,562

(22) PCT Filed: Dec. 22, 2005

(86) PCT No.: PCT/NO2005/000474
§ 371 (c)(1),
(2), (4) Date: Jun. 3, 2008

(87) PCT Pub. No.: WO2006/068500
PCT Pub. Date: Jun. 29, 2006

(65) Prior Publication Data
US 2009/0110597 A1 Apr. 30, 2009

(30) Foreign Application Priority Data
Dec. 23, 2004 (NO) .................................. 20045622

(51) Int. Cl.
*G01N 21/00* (2006.01)
(52) U.S. Cl. ............. 422/65; 422/63; 422/67; 422/68.1; 422/563; 422/119; 436/180
(58) Field of Classification Search .................... 422/63, 422/67, 68.1, 563, 119; 436/180
See application file for complete search history.

(56) References Cited

U.S. PATENT DOCUMENTS

| | | | |
|---|---|---|---|
| 4,034,700 A | 7/1977 | Bassett et al. | |
| 5,573,727 A | 11/1996 | Keefe | |
| 5,601,650 A | 2/1997 | Goldbecker et al. | |
| 6,076,583 A | 6/2000 | Edwards | |
| 6,626,224 B1 | 9/2003 | Ljungmann | |

FOREIGN PATENT DOCUMENTS

WO WO 03/089140 10/2003

*Primary Examiner* — Jyoti Nagpaul
(74) *Attorney, Agent, or Firm* — Frommer Lawrence & Haug LLP; Ronald R Santucci

(57) ABSTRACT

An apparatus for automatic execution of different treatment operations in connection with staining of tissue specimens on microscope slides, wherein the apparatus (1) comprises an assembly of vessels (4) for receiving different liquids for staining of the tissue specimens, a loading station (2) for microscope slides (28), a conveyor (5) for transfer of carriers with microscope slides from vessel to vessel in accordance with a treatment program, an unloading station (8) for treated microscope slides, and a control unit (18) for controlling the treatment operations in accordance with a data program. The apparatus comprises different levels (I, II) having units for execution of the relevant treatment operations. Thus, a first level (I) comprises the loading station (2) and the assembly of said vessels (4) with the appurtenant conveyor (5), and a second level (II) comprises a station (6) for application of cover glasses on the stained microscope slides (28), a succeeding station (7) for drying of the cover-slipped microscope slides, and the unloading station (8), a means (9) being provided for gripping and transfer of carriers (10) with stained microscope slides from the first level (I) to the cover-slipping station (6) on the second level (II).

18 Claims, 7 Drawing Sheets

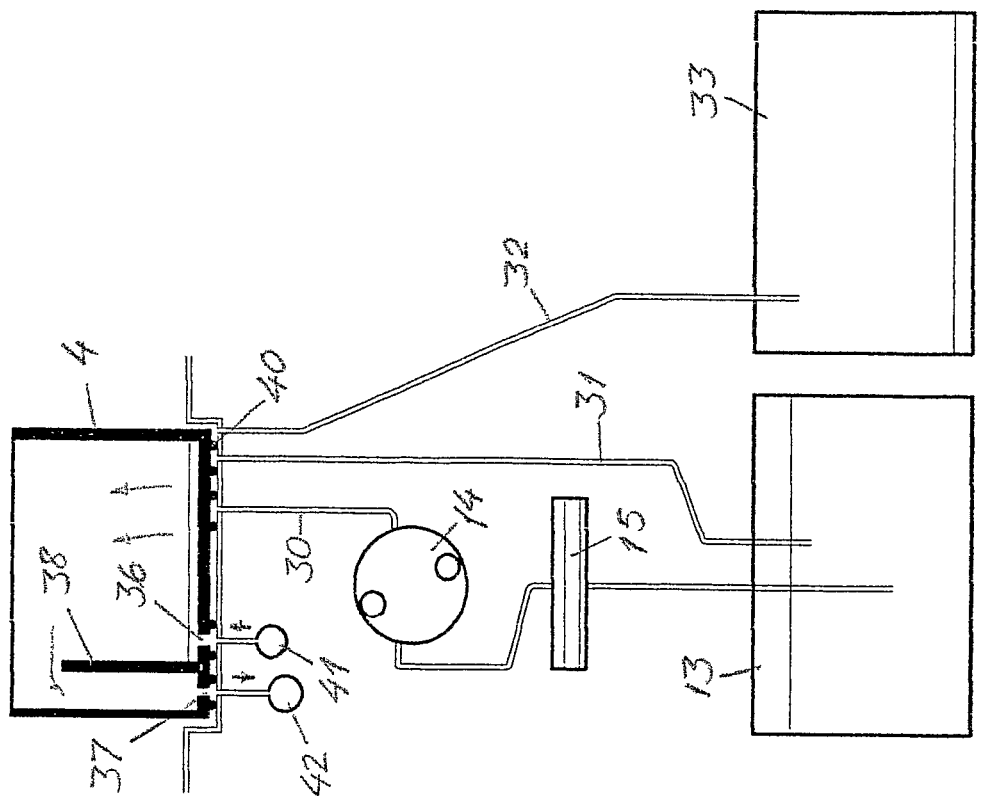
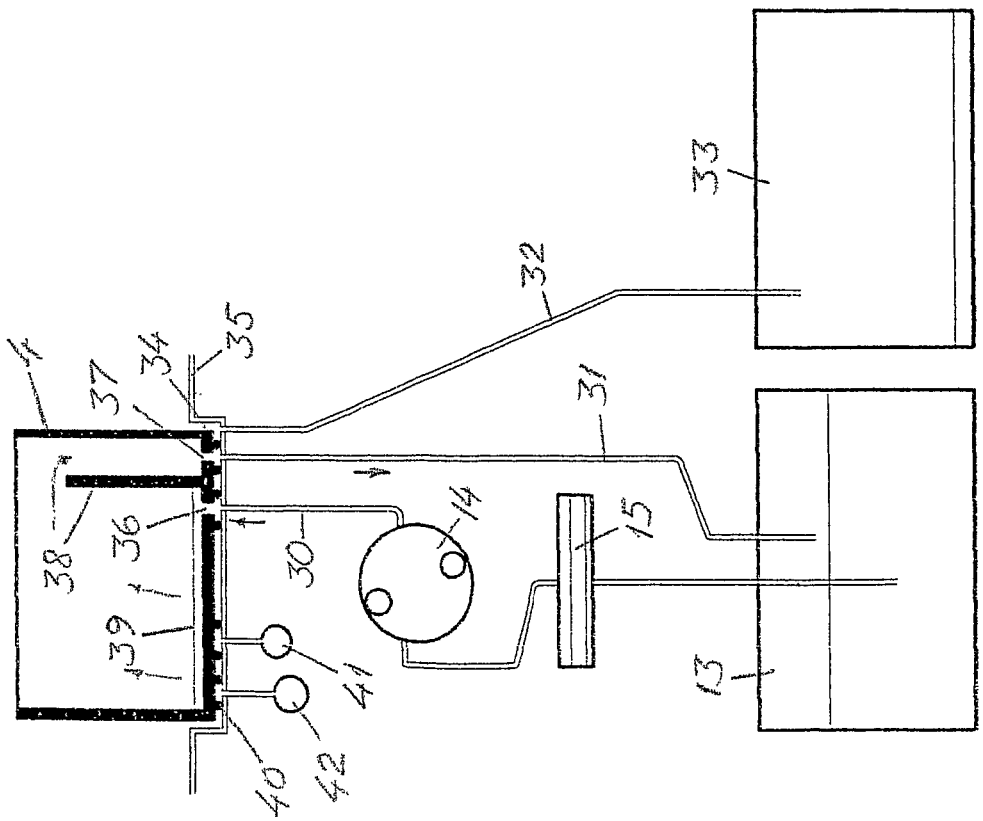

APPARATUS FOR EXECUTION OF TREATMENT OPERATIONS ON MICROSCOPE SLIDES WITH TISSUE SPECIMENS

This is a 371 filing of International Patent Application No. PCT/NO2005/000474 filed Dec. 22, 2005 and published on Jun. 29, 2006 under publication number WO 2006/068500 A and claims priority benefits from Norwegian Patent Application No. 20045622 filed Dec. 23, 2004, the disclosure of which is hereby incorporated by reference.

The invention relates to an apparatus for automatic execution of different treatment operations in connection with staining of tissue specimens on microscope slides, wherein the apparatus comprises an assembly of vessels for receiving different liquids for staining of the tissue specimens, a loading station for microscope slides, a conveyor for transfer of carriers with microscope slides from vessel to vessel in accordance with a treatment program, an unloading station for treated microscope slides, and a control unit for controlling the treatment operations in accordance with a data program.

There are previously known a number of different apparatuses of the above-mentioned type. As examples of prior art in this field reference can e.g. be made to U.S. Pat. No. 5,573,727 and U.S. Pat. No. 5,601,650. Both of these publications relate to apparatuses that are restricted to operations in connection with staining of tissue specimens on microscope slides. Thus, in the apparatus according to U.S. Pat. No. 5,601,650, the microscope slides are transported in microscope slide holders by means of a conveyor to treatment stations wherein they are subjected to treatment steps corresponding to a selectable staining process. The conveyor is constructed such that each microscope slide holder is separated therefrom after introduction into a treatment station, so that other microscope slide holders, in the course of the time a treatment operation is carried out at said treatment station, can be transported to free treatment stations in accordance with the selected staining process.

A main object of the invention is to provide a multi-function apparatus which is able to carry out many different operations in connection with treatment of tissue specimens on microscope slides.

An additional object of the invention is to provide such an apparatus which has a relatively compact construction.

The above-mentioned objects are achieved by means of an apparatus of the introductorily stated type which, according to the invention, is characterized in that the apparatus comprises different levels having units for execution of the relevant treatment operations, a first level comprising the loading station and the assembly of said vessels with the appurtenant conveyor, and a second level comprising a station for placing of cover glasses on the stained microscope slides, a succeeding station for drying of the cover-slipped microscope slides, and the unloading station, a means being provided for gripping and transfer of carriers with stained microscope slides from the first level to the cover slipping station on the second level.

With the apparatus according to the invention there can for example be carried out initial fixation of paraffin-embedded tissue specimens on microscope slides, staining of tissue specimens on microscope slides, mounting of cover glasses on stained tissue specimen microscope slides, and drying of stained tissue specimen microscope slides after application of glue and mounting of cover glasses, in accordance with a selected running process for the apparatus.

In an advantageous embodiment of the apparatus the carrier comprises an elongated hanger having a means for releasable clamping of the microscope slides in a hanging position with the surfaces located in a common plane. Such a carrier can be used during execution of all the relevant treatment operations, without manual handling or manipulation of the microscope slides.

In an additional advantageous embodiment of the apparatus according to the invention, wherein the apparatus comprises a plurality of tanks for the relevant liquids, wherein the tanks are connected with appurtenant vessels via line connections on which there are arranged pumps for the supply of liquid to the vessels, the control unit is arranged for selective control of the relevant pumps, so that a vessel to be used in a staining process, is filled with liquid at the start of the staining process, and such that the liquid-filled vessels are emptied automatically when they are no longer to be used in the staining process. Such an embodiment implies a particularly efficient utilization of the relevant treatment liquids. In addition there is achieved a substantial increase of the time between maintenance of the treatment liquids, a drastic reduction of the risk that operator personnel is subjected to dangerous fumes from the liquids, and avoidance of degradation of the liquids in that they are unnecessarily subjected to surrounding air.

Additional objects and advantages of the invention will appear from the following further description of exemplary embodiments with reference to the drawings, wherein FIG. 1 shows a principle drawing of an apparatus according to the invention;

FIGS. 3A and 3B show schematically an embodiment of an arrangement for supply of liquid from the tanks to the vessels in the apparatus, and for washing of the vessels with water;

Figure 1:
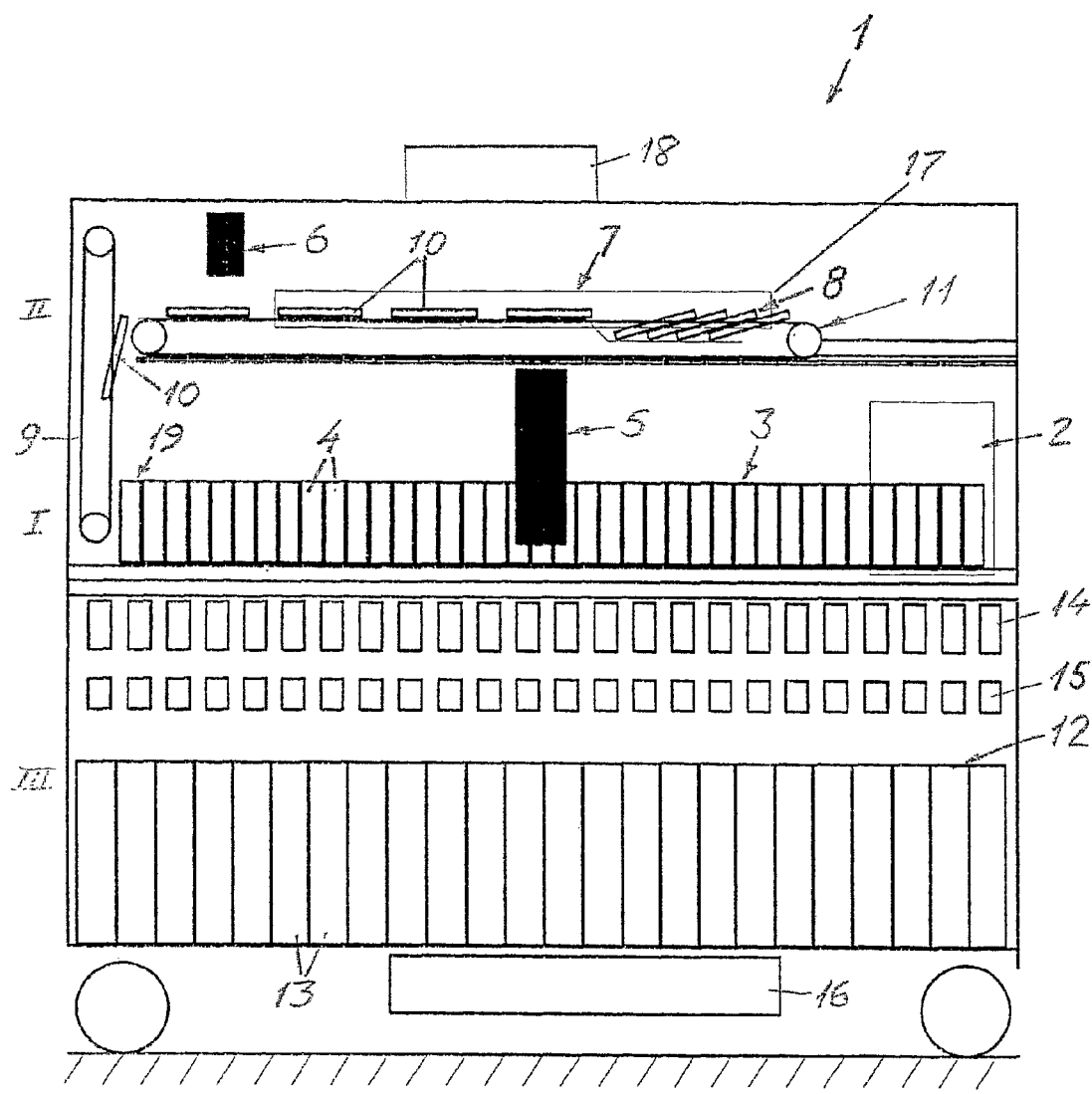

As appears from FIG. 1, the apparatus 1 according to the invention comprises three different levels, I, II and III, having units for execution of the relevant treatment operations.

The first level I includes a loading and preheating station 2 for microscope slides, a number of reagent stations 3 consisting of vessels 4 (see FIGS. 4 and 5) for staining of tissue specimens on microscope slides, and a conveyor 5 for transfer of carriers/holding devices with microscope slides from vessel to vessel in accordance with a selected treatment program.

The second level II includes a station 6 for application of cover glasses on the stained microscope slides, a succeeding drying station 7 and a storing/unloading station 8 for the ready-treated microscope slides. In the illustrated embodiment the second level II is located above the first level I, and a hoist or lifting means 9 is provided for transfer of carriers 10 with stained microscope slides from the first level to the cover glass applying or cover-slipping station 6 on the second level.

A horizontal transport means 11 is provided for transfer of carriers 10 with microscope slides through the cover-slipping station 6 and the drying station 7 to the unloading station 8.

The third level III includes an assembly 12 of a number of storage tanks 13 for the relevant reagent liquids, wherein the tanks are connected to appurtenant vessels 4 at the reagent stations 3 via connecting lines (not shown in FIG. 1) on which there are arranged pumps 14 for the supply of liquid to the vessels, and moreover filters 15 for filtering of the liquids. The arrangement for liquid supply and for washing of the vessels will be further described in connection with FIGS. 3A and 3B.

The apparatus in FIG. 1 is also shown to include a filter/blower unit 16 for ventilation of the apparatus. This unit is in communication with a vent inlet 17 at the top of the apparatus, and thereby provides for transport and blow-out of venting air through the apparatus. In this manner the whole apparatus is ventilated, so that i.a. dangerous fumes from the reagent stations are removed in a justifiable manner.

The apparatus also includes an electronic control unit which is symbolically shown as a block 18, and which takes care of controlling the treatment operations of the apparatus in accordance with a data program. Further, the apparatus comprises a control panel (not shown) for operation and working of the apparatus. This panel includes a number of touch or contact keys (control keys and working keys), and also a display giving information about the status etc. of the apparatus during operation.

As appears from FIG. 1, the vessels 4 at the reagent stations 3 are arranged in a single rectilinear row from the loading station 2 to a dedicated area 19 for transfer of carriers 10 with stained microscope slides from the first to the second level. The conveyor 5 which is to be further described in connection with FIG. 6, therefore needs to carry out only an xz-movement, i.e. movements only in a horizontal x-direction and a vertical z-direction.

The means 9 for gripping and transfer of carriers is only schematically shown in FIG. 1, and consists of a hoist for lifting of the carriers from the dedicated transfer area 19 to the second level II. As an alternative to such a lifting means, the transfer means may be arranged at the second level and arranged to fetch carriers 10 from the area 19 to the second level.

The station 6 for application of cover glasses on the stained microscope slides is also only schematically shown in FIG. 1. This station includes a number of elements, more specifically a cover glass magazine with a dispenser function, a glue pump, a glue dispenser and a unit for mounting of cover glasses on the supplied microscope slides with stained tissue specimens. Further, the station contains a detection unit for detection of microscope slides arriving at the station in the different supplied carriers. The cover glass magazine advantageously may be constructed for delivering cover glasses laterally from the bottom of the magazine. For a further description of such a station reference may e.g. be made to the international patent application No. PCT/NO99/00396 (WO 00/37986).

As appears from FIG. 1, the cover glass applying or cover-slipping station 6, the drying station 7 and the unloading station 8 are arranged in succession in a direction which is opposite to the direction from the loading station 2 to the means 9 for transfer of carriers from the first to the second level. In this manner there is obtained a compact apparatus with a little lateral extension.

As regards the loading and preheating station 2, this comprises a number of heated stations for fixation of paraffin on tissue specimen microscope slides, and in addition a number of liquid stations or empty stations for initial placing of carriers with microscope slides, were the different stations are used in accordance with the relevant or programmed treatment process that is to be used. The station 2 also includes a rush or emergency outlet station which is used for delivery of a carrier with microscope slides with tissue specimens to be analyzed immediately after a finished staining operation, without being provided with cover glasses over the tissue specimens. In such a case the control unit 18 will be programmed such that the conveyor with the carrier in question is directed to the rush output station.

Figure 2:
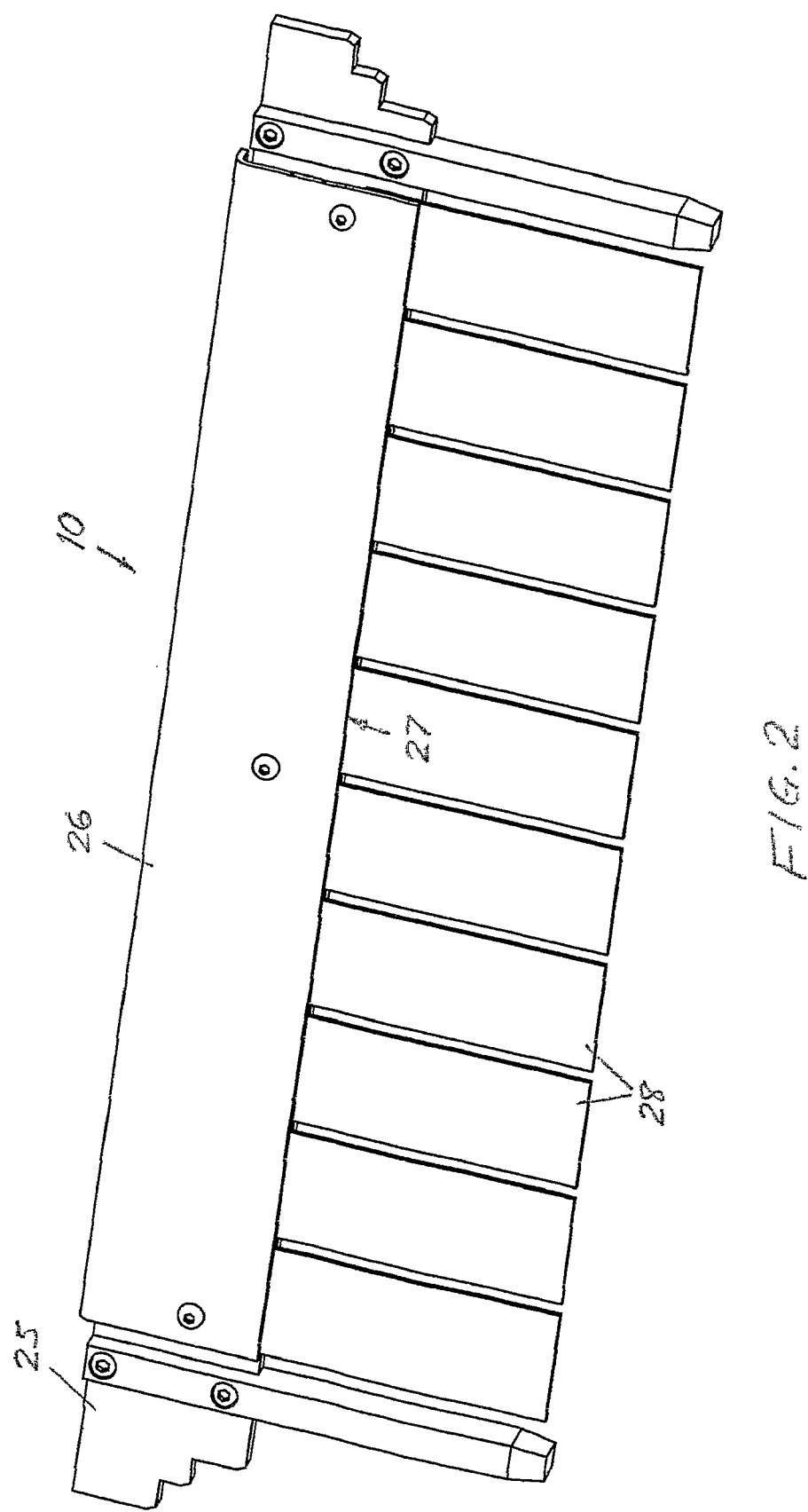
FIG. 2 shows a perspective view of a carrier or holding device for microscope slides, for use in the apparatus according to the invention.

An embodiment of the carrier/holding device 10 which is used in the apparatus according to the invention, is shown in FIG. 2.

As shown, the carrier 10 comprises an elongated hanger which in the illustrated embodiment consists of a carrier plate 25 on which there are mounted a spring-loaded clamp plate 26 which, in cooperation with the carrier plate, forms a clamp jaw 27 for releasable clamping of a number of microscope slides 28 in a hanging position with the surfaces of the microscope slides located in a common plane. In use of the hanger 10 with the clamped microscope slides, this is placed in the relevant vessel 4 with its longitudinal direction oriented transversely to the horizontal transport direction of the conveyor 5 from vessel to vessel. As appears from FIG. 1, the means 9 for gripping and transfer of carriers 10 is arranged to place the carrier/hanger with the microscope slides 28 in a horizontal lying position on the cover-slipping station 6. The above-mentioned detection unit on the station 6 can then in a safe manner detect the positions of the microscope slides in the carriers supplied to the station.

For a further description of the carrier/holding device 10 and its cooperation with a loading rack for loading of microscope slides, reference is made to the simultaneously filed patent application having the title "A holding device for microscope slides with tissue specimens".

An embodiment of an arrangement for liquid supply from the tanks 13 to the vessels 4 and for washing of the vessels with water, is shown in FIGS. 3A and 3B.

In the embodiment shown in FIG. 3A a pump 14 and a filter 15 are connected on a supply line 30. The pump preferably is of the peristaltic type, and it is preferably reversible, so that used reagent liquid can be returned to the vessel via the supply line 30. Further, a separate return line 31 is arranged between the vessel 4 and the tank 13, and an exhaust or outlet line 32 is arranged between the vessel and a waste tank 33.

The filters 15, which are arranged to secure the quality of the supplied liquids, are shown to be arranged at the suction side of the pumps 14. However, they can with advantage be located on the pumping side of the pumps, to achieve the best possible pumping efficiency.

As further appears from FIG. 3A, each of the reagent vessels 4 in the apparatus in FIG. 1 is placed in an appurtenant recess 34 in a carrier plate 35 arranged in the apparatus. The vessel 4 in the figure is shown in longitudinal section. The vessel is provided with an inlet opening 36 in the bottom of the vessel at one end of the vessel, and with an outlet opening 37 in the bottom of the vessel at an opposite side of an overflow wall 38 in relation to the inlet opening 36, the arrangement being such that a through-flow of liquid is produced through the vessel with continuous supply of liquid to the vessel by means of the relevant pump. The through-flow is obtained in that a perforated spreading plate 39 is placed above the bottom of the vessel, so that liquid flowing into the vessel is distributed over the bottom of the vessel below the spreading plate 39, before the liquid flows through the holes in the spreading plate and thereby causes a through-flow of liquid through the whole vessel before it flows over the overflow wall 38 and out of the vessel.

The vessels 4 are releasable mounted in the recesses 39 in the carrier plate 35, and the inlet and outlet openings 36 respectively 37 of the vessels are connected in a sealing manner to the connecting lines 30 and 31 by means of O-ring seals 40 which are clamped between the underside of the vessels 4 and the bottom of the recesses 34 when the vessels are put in place in the recesses.

A appears from FIGS. 3A and 3B, a water inlet 41 and a water outlet 42 are arranged in the bottom of the recess 34 at the opposite side of the recess in relation to the inlet for the connecting line 30 and the outlet for the return line 31. The water inlet 41 and the inlet from the connecting line 30 are arranged symmetrically about a midpoint of the vessel, and the same is the case with the water outlet 42 in relation to the return line 31. By mounting the vessels 4 in the apparatus in a reversed position, i.e. turned 180° relative to the normal operating position in FIG. 3A, it is thereby achieved that the vessels are connected automatically to a system for flushing and cleaning of the vessels with water. This position of the vessel 4 is shown in FIG. 3B. Thus, by means of this arrangement the vessels can be flushed and cleaned without being removed from the apparatus.

If the O-ring seals 40 in the recess 34 should not be quite tight, possible leaked-out liquid will be directed from the recess to the waste tank 33 by means of the outlet line 32.

In the embodiment shown in FIG. 3A, the vessel 4 is supplied with reagent liquid from a single appurtenant tank 13. However, a vessel 4 may be supplied with liquid from several tanks in that the connecting lines from these tanks are coupled to a multi-way valve connecting the tank containing the relevant liquid. For a further description of such alternative embodiments reference is made to the simultaneously filed international patent application having the title "Method and system for use of treatment liquids in an apparatus for staining of tissue specimens on microscope slides".

Figure 4:
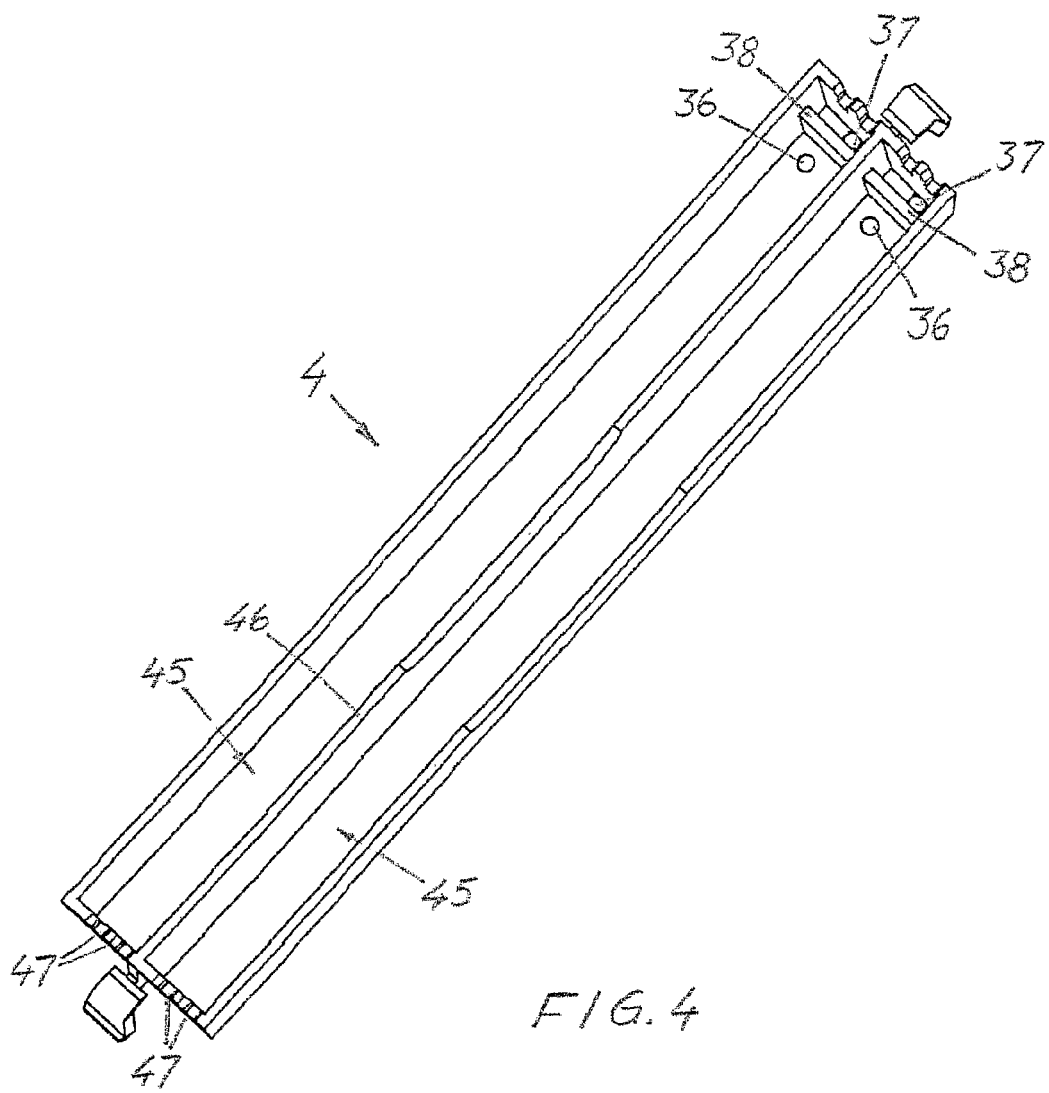
FIG. 4 shows a perspective view seen from above of a vessel arranged for releasable mounting at a treatment station in the apparatus of FIG. 1.

A vessel 4 which is arranged for releasable mounting at a staining station in the apparatus of FIG. 1, is shown in FIG. 4. The vessel has an elongated shape and is divided into two parallel spaces 45 by means of a longitudinally extending partition 46. As mentioned above in connection with FIG. 3A, each space 45 is provided with an inlet opening 36 in the bottom of the vessel at one end of the vessel, and with an outlet opening 37 in the bottom the vessel at an opposite side of an overflow wall 38 in relation to the inlet opening 36.

Each of the end walls of the vessel 4 is provided with four notches 47 for receiving suspension portions at the ends of carriers/holding devices for microscope slides. As mentioned above, these holding devices are further described in the simultaneously filed international patent application having the title "A holding device for microscope slides with tissue specimens".

Figure 5:
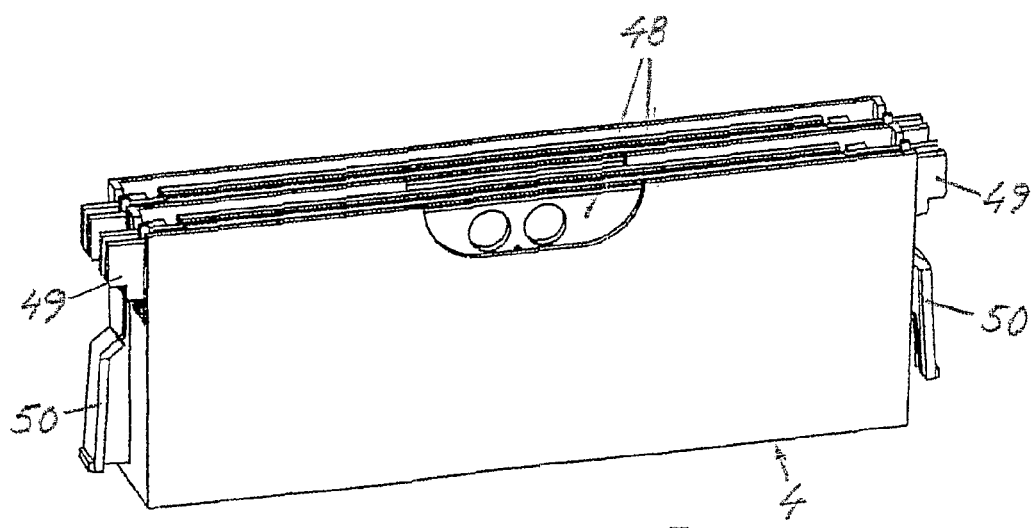
FIG. 5 shows a perspective view of the vessel in FIG. 4, wherein holding devices with microscope slides are placed in the vessel.

FIG. 5 shows a perspective view of a vessel 4 in which there are placed four holding devices 48, the suspension portions 49 of the holding devices being placed in respective ones of said notches 47. As further appears, the vessel at its ends is provided with fastening members 50 and 51 for releasable mounting of the vessel at the relevant reagent station in the apparatus 1. The fastening member 50 is here a fixed member, whereas the fastening member 51 is resilient, to allow a resilient fixing thereof.

Figure 6:
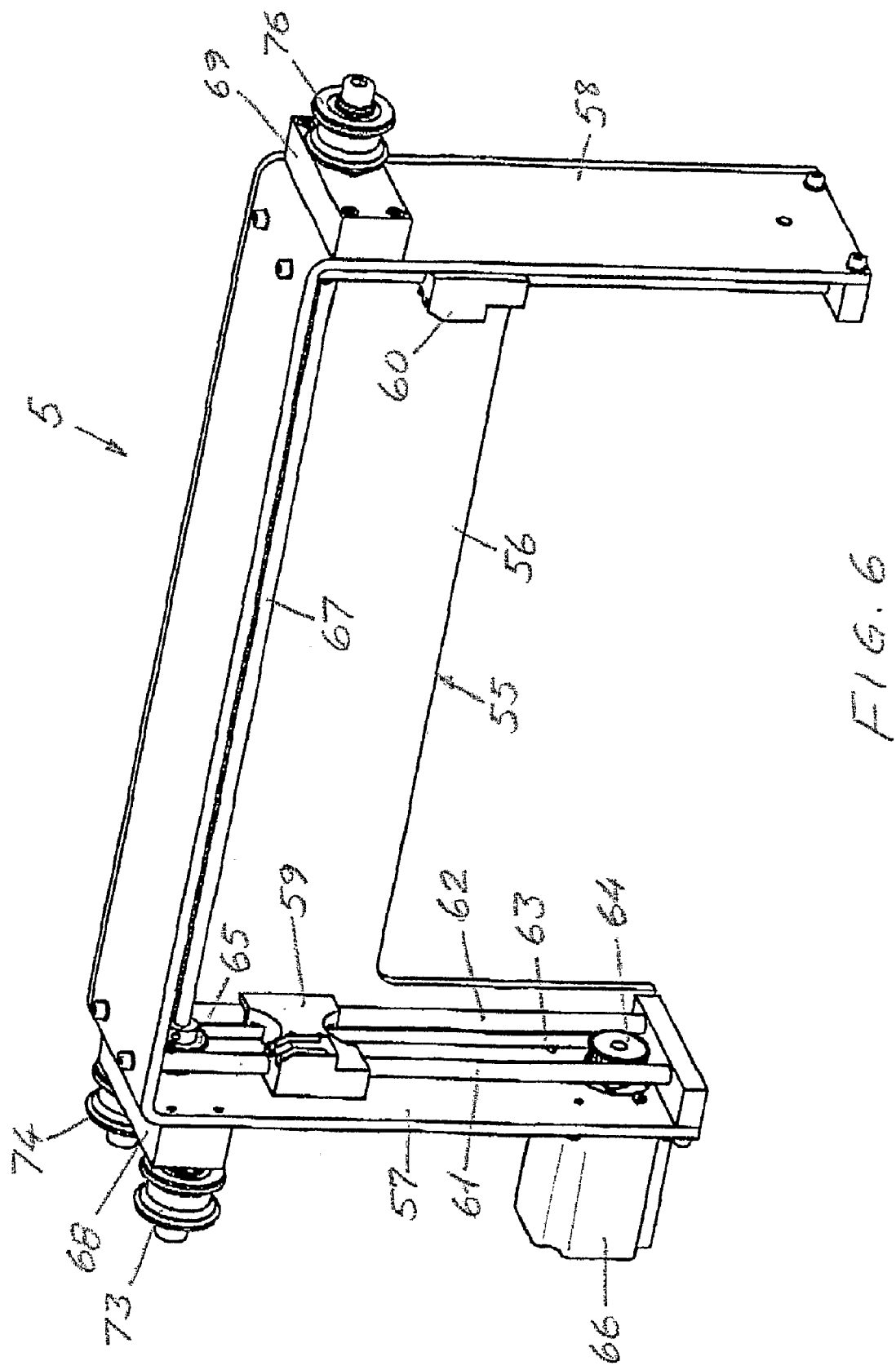
FIG. 6 shows a perspective view of a conveyor for use in the apparatus of FIG. 1.
Figure 8:
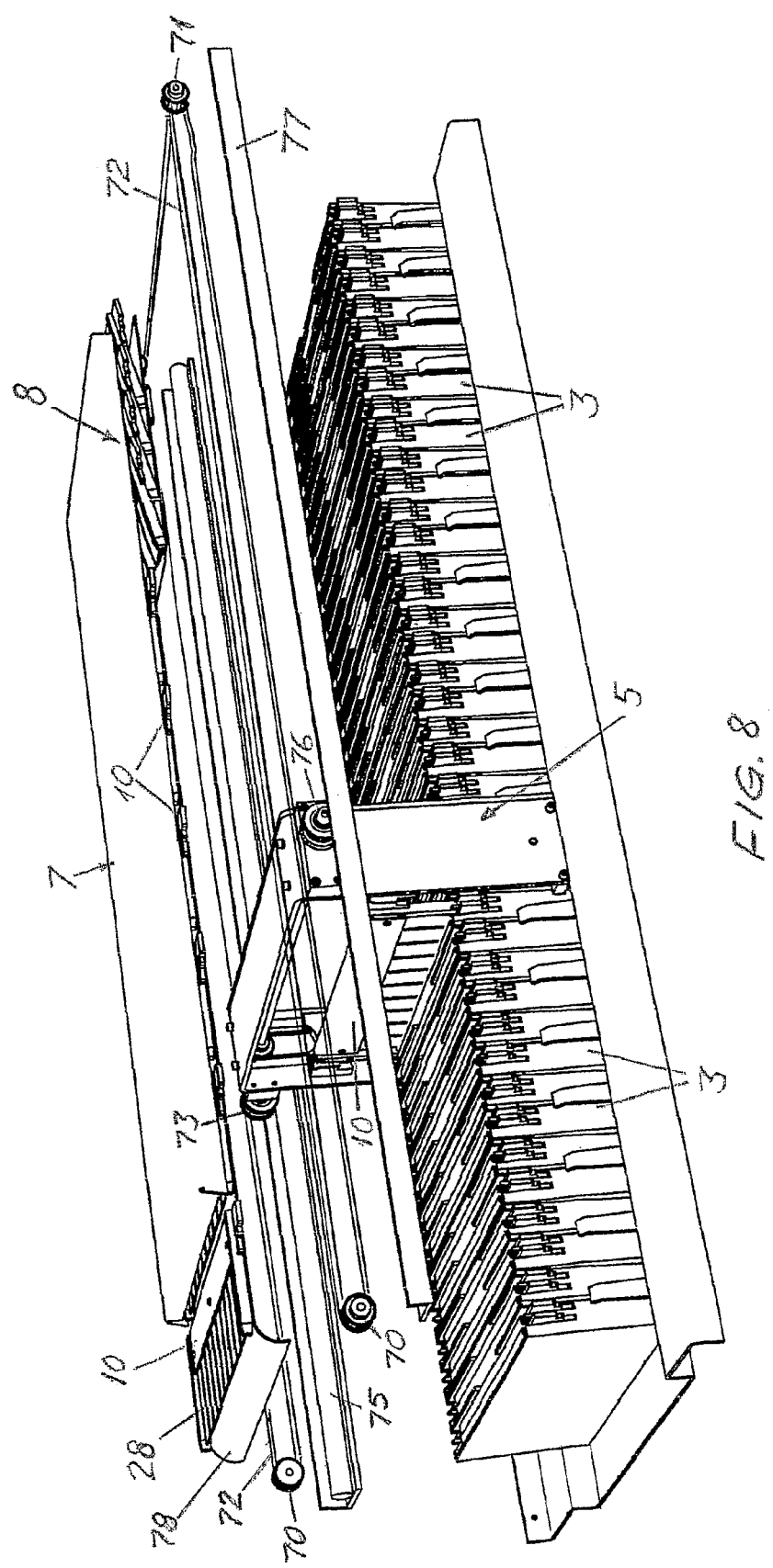
FIG. 8 is a perspective view showing the row of staining/reagent stations in the apparatus and the conveyor thereof, and also partly the additional stations arranged above the reagent stations for treatment of microscope slides with tissue specimens.

FIG. 6 shows an embodiment of a conveyor 5 for use in the apparatus of FIG. 1. The conveyor 5 comprises an inverted U-shaped or portal-like main body 55 consisting of a transverse member 56 extending above and parallel with the reagent stations 3 of the apparatus, and a pair of side members 57 respectively 58 located at a little distance outside of the reagent stations at each end thereof, as shown in FIG. 8. At the inside of each of the side members 57, 58 there is mounted a lifting means 59 respectively 60 which is adapted to lift one or two carriers 10 with microscope slides. Each lifting means is slidably mounted on a pair of vertical guide columns 61, 62, and can be lifted or lowered on the guide columns by means of a toothed belt 63 running over a lower and an upper toothed belt wheel 64 respectively 65 mounted in the side member 57. The lower wheel 64 is driven by a step motor 66. The drive movement is transferred from the upper toothed belt wheel 65 via a transfer shaft 67 to a corresponding toothed belt drive (not visible in FIG. 6) mounted on the other side member 58.

The conveyor further comprises a pair of fixing blocks 68 and 69 for horizontal toothed belt drive of the conveyor, i.e. for the program-controlled movement of the conveyor in the x-direction transversely to the reagent stations 3. This toothed belt drive is schematically shown in FIG. 8 where there are shown a pair of toothed belt wheels 70, 71 with appurtenant toothed belts 72.

In its horizontal movement the conveyor is guided by a pair of running wheels 73, 74 mounted on the fixing block 68 on the side member 57 and running along a guide rod 75 (see FIG. 8), and a running wheel 76 mounted on the fixing block 69 on the side member 58 and running on an angular rail 77.

Figure 7:
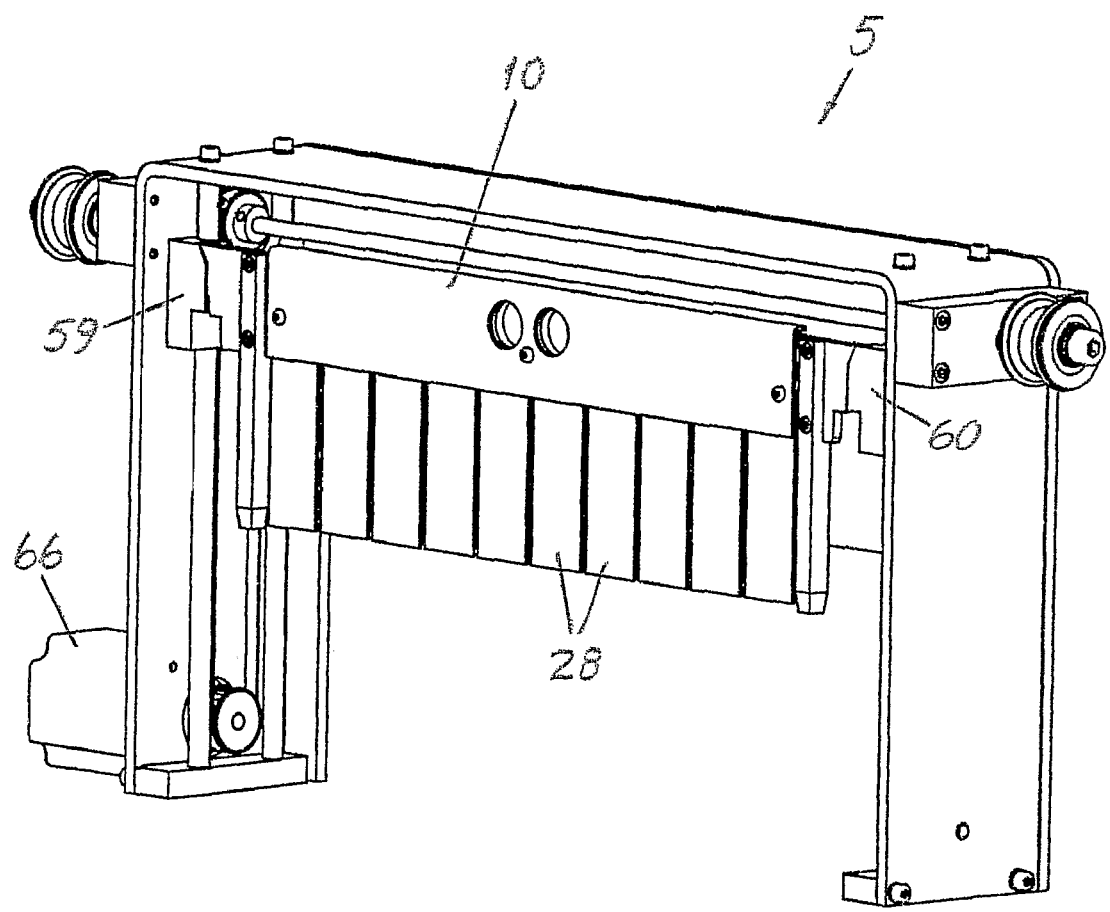
FIG. 7 shows the conveyor in FIG. 6 wherein a holding device with microscope slides are suspended from the conveyor.

FIG. 7 shows the conveyor 5 in FIG. 6, wherein a carrier/holding device 10 with microscope slides 28 are suspended from the lifting means 59 and 60 of the carrier.

The schematic perspective view in FIG. 8 also shows a part of the stations arranged at the second level II above the reagent stations 3 and the conveyor 5 at the first level I, more specifically the drying station 7 and the storage/unloading station 8. The horizontal transport means 11 shown in FIG. 1, is left out in FIG. 8. The figure shows an entry portion 78 of a sliding plate where a carrier 10 with microscope slides 28 is supplied to a horizontally lying position at the station 6, ready for application of cover glasses on the microscope slides. The sliding plate extends through the station 6 (not further shown in FIG. 8) and the drying station 7 and is terminated at the storage and unloading station 8.

As further appears from the figure, the transport means advances the carriers 10 with cover-slipped microscope slides through the drying station 7 to the station 8 where the carriers are stored for unloading in a stack wherein the carriers rest partly on each other in a slanting position (at an angle of about 10° with the horizontal).

A complete operational sequence in operation of the apparatus according to the invention will be described below.

At the start of an operational sequence one or more carriers/holding devices are loaded into a dedicated area of the loading station, dependent on the types of tissue specimens being on the microscope slides in the carrier. One area of the loading station may be dedicated for fixation of paraffin-embedded tissue specimens on microscope slides, and another area may be liquid vessels for other tissue specimens. The operator thereafter will select a program for an inserted carrier. Alternatively the carrier may be able to be started automatically in accordance with a selected standard program.

After insertion in the loading area the carrier will remain in this area in accordance with a programmed time or according to the finishing intervals of the total process. The carrier thereafter is moved automatically from the loading station to the second step in the treatment operation by means of the conveyor. The vessel for this step will be supplied with liquid from a tank through the pumping system connected to the vessel, so that the vessel will be liquid-filled at the time when tissue specimens on the microscope slides in the carrier are placed in the vessel. In order to get a good and efficient treatment operation, there will be supplied a flow of liquid which can be adjusted by means of speed adjustment of the motor of the pump. When the time criterion in this step is satisfied in accordance with a given protocol, the vessel may be emptied and filled with a new liquid in accordance with the protocol by filling of a new liquid from another connected tank via a valve connected to the same vessel, or the conveyor may move the carrier to a new vessel dependent on how the apparatus is set up, in order to give a shortest possible throughput speed. These transfers of carriers in accordance with different protocols and control of the supply into and out of vessels with one or more reagents, take place continuously so that each carrier will have been placed at the correct time in each liquid in accordance with its protocol. During running the apparatus will register through-flown liquid quantity in connection with the effective life of the liquid, to thereby be able to give a warning when the different liquids are to be replaced. This takes place at the same time as more carriers can be loaded into the loading station.

When a carrier has been delivered to the dedicated transfer area, the transfer means of the apparatus will transfer the carrier to the cover-slipping station for application of glue and cover glasses on the microscope slides detected in the carrier. This takes place at the same time as carriers can be loaded into the loading station, and at the same time as other carriers are treated in liquids in accordance with their protocol.

By means of the transport means at the second level of the apparatus the ready-stained and mounted tissue specimen microscope slides located in the carrier will be transported through the drying station, so that solvent being on the microscope slides/-cover glasses will be dried away, whereafter the carrier in question will be transported to the delivery station.

The invention claimed is:

1. An apparatus for automatic execution of different treatment operations in connection with staining of tissue specimens on microscope slides, wherein the apparatus comprises an assembly of vessels for receiving different liquids for staining of the tissue specimens, a loading station for microscope slides, a conveyor for transfer of carriers with microscope slides from vessel to vessel in accordance with a treatment program, an unloading station for treated microscope slides, and a control unit for controlling the treatment operations in accordance with a data program, wherein the apparatus comprises separate levels (I, II) having associated units for execution of the relevant treatment operations, a first level (I) comprising the loading station and the assembly of said vessels with the appurtenant conveyor, and a second level (II) comprising a station for application of cover glasses on the stained microscope slides, a succeeding station for drying of the cover-slipped microscope slides, and the unloading station, a means being provided for gripping and transfer of carriers with stained microscope slides from the first level (I) to the cover-slipping station on the second level (II), the vessels being arranged in a single rectilinear row from the loading station to a dedicated area for transfer of carriers with stained microscope glasses from the first to the second level, the conveyor comprising a carrier-lifting means arranged to carry out an xz-movement, i.e. movements only in a horizontal x-direction and a vertical z-direction, and the cover-slipping station, the drying station and the unloading station being arranged in succession in a direction which is opposite to the direction from the loading station to the means for transfer of carriers from the first (I) to the second (II) level.

2. An apparatus according to claim 1, wherein the second level (II) is located above the first level (I).

3. An apparatus according to claim 1, wherein the carrier comprises an elongated hanger having a means for releasable clamping of the microscope slides in a hanging position with the surfaces located in a common plane.

4. An apparatus according to claim 3, wherein the hanger with the clamped microscope slides is placed in the relevant vessel with its longitudinal direction oriented transversely to the horizontal transport direction (the x-direction) of the conveyor from vessel to vessel.

5. An apparatus according to claim 4, wherein the conveyor comprises a portal-like main body extending above and parallel with the vessels, the carrier-lifting means being arranged under the carriers and arranged for lifting and lowering of the relevant carriers by vertical movement in a movement region at the underside of the carriers.

6. An apparatus according to claim 4, wherein the means for gripping and transfer of carriers is arranged to place the hanger with the microscope slides in a horizontal, lying position on the cover-slipping station.

7. An apparatus according to claim 1, wherein the means for gripping and transfer of carriers is a hoisting means for lifting of the carriers from the dedicated transfer area to the second level (II).

8. An apparatus according to claim 1, wherein the means for gripping and transfer of the carriers is arranged at the second level (II) and is arranged to fetch the carriers from the dedicated transfer area to the second level.

9. An apparatus according to claim 1, wherein it includes a plurality of tanks for the relevant liquids, the tanks being connected to appurtenant vessels via line connections on which there are arranged pumps for supply of liquid to the vessels.

10. An apparatus according to claim 9, wherein the pumps are reversible peristaltic pumps.

11. An apparatus according to claim 9, wherein the tanks are arranged on a third level (III) located below the first level (I).

12. An apparatus according to claim 9, wherein the control unit is arranged for selective control of the relevant pumps, so that a vessel to be used in a staining process, is filled with liquid at the start of the staining process, and so that the liquid-filled vessels are emptied automatically when they are no longer to be used in the staining process.

13. An apparatus according to claim 9, wherein at least some of the vessels are provided with at least one inlet opening in the bottom of the vessel at an end of the vessel, and with at least one outlet opening in the bottom of the vessel at an opposite side of an overflow wall in relation to the inlet opening, in such a manner that a through-flow of liquid is produced through the vessel with continuous supply of liquid to the vessel by means of the relevant pump.

14. An apparatus according to claim 9, wherein at least some of the vessels are reversibly mounted in the apparatus, and further are clamped to their line connections in a sealing manner, the arrangement being such that said vessels, when mounted in the apparatus in a position in which the vessels are turned 180° relative to the normal operating position, are automatically connected with a cleaning system for flushing and cleaning of the vessels.

15. An apparatus according to claim 9, wherein the vessels have an elongated shape and are divided in two parallelly extending spaces by means of an intermediate partition, each space being dimensioned and adapted for receipt of two juxtaposed carriers with appurtenant microscope slides.

16. An apparatus according to claim 9, wherein the cover-slipping station is provided with a detection unit for detection of microscope to slides supplied to the station from the first level (I).

17. An apparatus according to claim 9, wherein the cover-slipping station comprises a magazine for cover glasses, a glue pump, a glue dispenser and a unit for mounting of cover glasses on the supplied microscope slides with stained tissue specimens.

18. An apparatus according to claim 9, wherein it includes a horizontal transport means arranged on the second level (II) and extending from the cover-slipping station and through the drying station to the unloading station.

* * * * *